US008608686B2

(12) United States Patent
Tennican et al.

(10) Patent No.: US 8,608,686 B2
(45) Date of Patent: Dec. 17, 2013

(54) SYRINGE DEVICES, COMPONENTS OF SYRINGE DEVICES, AND METHODS OF FORMING COMPONENTS AND SYRINGE DEVICES

(75) Inventors: Patrick O. Tennican, Spokane, WA (US); L. Myles Phipps, Shelton, WA (US)

(73) Assignee: Hyprotek, Inc., Spokane, WA (US)

( * ) Notice: Subject to any disclaimer, the term of this patent is extended or adjusted under 35 U.S.C. 154(b) by 0 days.

(21) Appl. No.: 13/399,767

(22) Filed: Feb. 17, 2012

(65) Prior Publication Data

US 2012/0150146 A1     Jun. 14, 2012

Related U.S. Application Data

(63) Continuation of application No. 11/558,146, filed on Nov. 9, 2006, now Pat. No. 8,137,307.

(60) Provisional application No. 60/735,481, filed on Nov. 9, 2005, provisional application No. 60/763,647, filed on Jan. 30, 2006.

(51) Int. Cl.
*A61M 37/00* (2006.01)

(52) U.S. Cl.
USPC .......................................................... 604/89

(58) Field of Classification Search
USPC ........................................ 604/89–91, 167.05
See application file for complete search history.

(56) References Cited

U.S. PATENT DOCUMENTS

| | | |
|---|---|---|
| 730,054 A | 6/1903 | Sheets |
| 984,037 A | 2/1911 | Sheets |
| 1,100,799 A | 6/1914 | Wedig |
| 1,465,793 A | 8/1923 | Schilling |
| 1,696,018 A | 12/1928 | Schellberg |
| 1,707,880 A | 4/1929 | Sheets |
| 2,453,590 A | 11/1948 | Poux |
| 2,540,461 A | 2/1951 | Smith |

(Continued)

FOREIGN PATENT DOCUMENTS

| | | |
|---|---|---|
| CA | 2513165 A1 | 8/2004 |
| JP | 01-131671 | 5/1989 |

(Continued)

OTHER PUBLICATIONS

EP 08836593 Supplemental SR, Apr. 17, 2012, Hyprotek.

(Continued)

*Primary Examiner* — Nicholas Lucchesi
*Assistant Examiner* — Nathan R Price
(74) *Attorney, Agent, or Firm* — Wells St. John P.S.

(57) ABSTRACT

A syringe device includes a syringe barrel and piston having a fluid passageway extending from a vial port. Another syringe device includes a syringe barrel, a piston sleeve and an insert. A channel extends along a side of the insert. A valve controls fluid communication between the channel and the syringe barrel. Another syringe device has a syringe barrel, a piston sleeve and an insert. A valve controls fluid communication between a compartment within the insert and the syringe barrel. A method of preparing a medication includes providing a component within a syringe barrel and another component within a compartment of a piston insert. A seal is over-molded onto a tip of the insert and an end of a piston sleeve. The sleeve is rotated relative to the insert to establish fluid communication between the compartment and the barrel chamber.

2 Claims, 14 Drawing Sheets

(56) References Cited

U.S. PATENT DOCUMENTS

| | | |
|---|---|---|
| 2,555,878 A | 6/1951 | Drabicki |
| 2,661,740 A | 12/1953 | Hickey |
| 2,677,372 A | 5/1954 | Barnish |
| 2,693,186 A | 11/1954 | Riker et al. |
| 2,818,999 A | 1/1958 | Miller |
| 2,842,124 A | 7/1958 | James |
| 2,869,544 A | 1/1959 | Ratcliff et al. |
| 3,052,239 A | 9/1962 | Silver et al. |
| 3,052,240 A | 9/1962 | Silver et al. |
| 3,164,303 A | 1/1965 | Trautmann |
| 3,342,180 A | 9/1967 | Sandhage et al. |
| 3,348,546 A | 10/1967 | Roberts et al. |
| 3,473,646 A | 10/1969 | Burke |
| 3,551,239 A | 12/1970 | Tuschhoff |
| 3,645,268 A | 2/1972 | Capote |
| 3,648,704 A | 3/1972 | Jackson |
| 3,659,602 A | 5/1972 | Cloyd |
| 3,841,329 A | 10/1974 | Killinger |
| 3,844,318 A | 10/1974 | Raia et al. |
| 3,938,520 A | 2/1976 | Scislowicz et al. |
| 3,946,732 A | 3/1976 | Hurscham |
| 4,014,330 A | 3/1977 | Genese |
| 4,031,892 A | 6/1977 | Hurschman |
| 4,044,757 A | 8/1977 | McWhorter et al. |
| 4,116,240 A | 9/1978 | Guiney |
| 4,142,633 A | 3/1979 | Raghavachari et al. |
| 4,153,057 A | 5/1979 | Kobel |
| 4,164,203 A | 8/1979 | Cavanagh |
| 4,166,533 A | 9/1979 | Maitland |
| 4,191,225 A | 3/1980 | Ogle |
| 4,244,364 A | 1/1981 | Grushkin |
| 4,303,069 A | 12/1981 | Cohen |
| 4,328,802 A | 5/1982 | Curley et al. |
| 4,405,317 A | 9/1983 | Case |
| 4,411,662 A | 10/1983 | Pearson |
| 4,424,057 A | 1/1984 | House |
| 4,464,174 A | 8/1984 | Ennis |
| 4,518,386 A | 5/1985 | Tartaglia |
| 4,585,446 A | 4/1986 | Kempf |
| 4,589,879 A | 5/1986 | Pearson |
| 4,591,357 A | 5/1986 | Sneider |
| 4,599,082 A | 7/1986 | Grimard |
| 4,624,667 A | 11/1986 | Rutnarak |
| 4,657,534 A | 4/1987 | Beck et al. |
| 4,685,596 A | 8/1987 | Mattheis |
| 4,700,872 A | 10/1987 | Keyes et al. |
| 4,722,733 A | 2/1988 | Howson |
| 4,735,608 A | 4/1988 | Sardam |
| 4,758,231 A | 7/1988 | Haber et al. |
| 4,759,750 A | 7/1988 | DeVries et al. |
| 4,781,701 A | 11/1988 | Geprags |
| 4,838,855 A | 6/1989 | Lynn |
| 4,861,335 A | 8/1989 | Reynolds |
| 4,874,381 A | 10/1989 | Vetter |
| 4,886,495 A | 12/1989 | Reynolds |
| 4,898,209 A | 2/1990 | Zbed |
| 4,915,701 A | 4/1990 | Halkyard |
| 4,969,883 A | 11/1990 | Gilbert et al. |
| 4,994,029 A | 2/1991 | Rohrbough |
| 4,997,420 A | 3/1991 | Lefevre |
| 5,067,948 A | 11/1991 | Haber et al. |
| 5,069,670 A | 12/1991 | Vetter et al. |
| 5,080,649 A | 1/1992 | Vetter |
| 5,098,402 A | 3/1992 | Davis |
| 5,135,496 A | 8/1992 | Vetter et al. |
| 5,137,511 A | 8/1992 | Reynolds |
| 5,139,490 A | 8/1992 | Vetter et al. |
| 5,147,329 A | 9/1992 | Brannon |
| 5,171,214 A | 12/1992 | Kolber et al. |
| 5,181,909 A | 1/1993 | McFarlane |
| 5,226,900 A | 7/1993 | Bancsi et al. |
| 5,247,972 A | 9/1993 | Tetreault |
| 5,290,228 A | 3/1994 | Uemura et al. |
| 5,312,336 A | 5/1994 | Haber et al. |
| 5,320,603 A | 6/1994 | Vetter et al. |
| 5,330,426 A | 7/1994 | Kriesel et al. |
| 5,334,163 A | 8/1994 | Sinnett |
| 5,356,375 A | 10/1994 | Higley |
| 5,356,380 A | 10/1994 | Hoekwater et al. |
| 5,364,369 A | 11/1994 | Reynolds |
| 5,372,586 A | 12/1994 | Haber et al. |
| 5,372,590 A | 12/1994 | Haber et al. |
| 5,393,497 A | 2/1995 | Haber et al. |
| 5,407,070 A | 4/1995 | Bascos et al. |
| 5,411,489 A | 5/1995 | Pagay et al. |
| 5,411,499 A | 5/1995 | Dudar et al. |
| 5,423,751 A | 6/1995 | Harrison et al. |
| 5,437,648 A | 8/1995 | Graves et al. |
| 5,466,219 A | 11/1995 | Lynn et al. |
| 5,466,220 A | 11/1995 | Brenneman |
| 5,470,327 A | 11/1995 | Halgren et al. |
| 5,472,403 A | 12/1995 | Cornacchia et al. |
| 5,478,314 A | 12/1995 | Malenchek |
| 5,478,337 A | 12/1995 | Okamoto et al. |
| 5,484,406 A | 1/1996 | Wong et al. |
| 5,489,266 A | 2/1996 | Grimard |
| 5,505,704 A | 4/1996 | Pawelka et al. |
| 5,529,189 A | 6/1996 | Feldschuh |
| 5,531,672 A | 7/1996 | Lynn |
| 5,531,683 A | 7/1996 | Kriesel et al. |
| 5,533,994 A | 7/1996 | Meyer |
| 5,549,569 A | 8/1996 | Lynn et al. |
| 5,566,729 A | 10/1996 | Grabenkort et al. |
| 5,569,191 A | 10/1996 | Meyer |
| 5,569,193 A | 10/1996 | Hofstetter et al. |
| 5,580,351 A | 12/1996 | Helgren et al. |
| 5,584,819 A | 12/1996 | Kopfer |
| 5,618,268 A | 4/1997 | Raines et al. |
| 5,630,800 A | 5/1997 | Blank et al. |
| 5,637,100 A | 6/1997 | Sudo |
| 5,647,845 A | 7/1997 | Haber et al. |
| 5,653,686 A | 8/1997 | Coulter et al. |
| 5,674,195 A | 10/1997 | Truthan |
| 5,685,866 A | 11/1997 | Lopez |
| 5,722,950 A | 3/1998 | Fujita et al. |
| 5,738,655 A | 4/1998 | Vallelunga et al. |
| 5,766,147 A | 6/1998 | Sancoff et al. |
| 5,769,825 A | 6/1998 | Lynn |
| 5,772,665 A | 6/1998 | Glad et al. |
| 5,776,125 A | 7/1998 | Dudar et al. |
| 5,785,701 A | 7/1998 | Sams et al. |
| 5,795,337 A | 8/1998 | Grimard |
| 5,807,323 A | 9/1998 | Kriesel et al. |
| 5,827,262 A | 10/1998 | Neftel et al. |
| 5,833,653 A | 11/1998 | Vetter et al. |
| 5,842,326 A | 12/1998 | Wolf |
| 5,897,527 A | 4/1999 | Tsukada |
| 5,928,215 A | 7/1999 | Caizza et al. |
| RE36,273 E | 8/1999 | Brannon |
| 5,976,115 A | 11/1999 | Parris et al. |
| 5,989,227 A | 11/1999 | Vetter et al. |
| 6,027,472 A | 2/2000 | Kriesel et al. |
| 6,065,270 A | 5/2000 | Reinhard et al. |
| 6,099,511 A | 8/2000 | Devos et al. |
| 6,149,623 A | 11/2000 | Reynolds |
| 6,267,154 B1 | 7/2001 | Felicelli et al. |
| 6,280,430 B1 | 8/2001 | Neftel et al. |
| 6,319,225 B1 | 11/2001 | Sugita et al. |
| 6,349,850 B1 | 2/2002 | Cheikh |
| 6,358,236 B1 | 3/2002 | DeFoggi et al. |
| 6,364,866 B1 | 4/2002 | Furr et al. |
| 6,379,328 B1 | 4/2002 | Mac Clay |
| 6,379,340 B1 | 4/2002 | Zinger et al. |
| 6,391,014 B1 | 5/2002 | Silverman |
| 6,478,788 B1 | 11/2002 | Aneas |
| 6,478,808 B2 | 11/2002 | Nowakowski |
| 6,488,651 B1 | 12/2002 | Morris et al. |
| 6,491,665 B1 | 12/2002 | Vetter et al. |
| 6,527,738 B1 | 3/2003 | Jones et al. |
| 6,544,233 B1 | 4/2003 | Fukui et al. |
| 6,576,224 B1 | 6/2003 | Osbakken et al. |
| 6,591,876 B2 | 7/2003 | Safabash |
| 6,599,264 B1 | 7/2003 | Erni et al. |
| 6,599,273 B1 | 7/2003 | Lopez |

(56) References Cited

U.S. PATENT DOCUMENTS

| | | |
|---|---|---|
| 6,602,223 B2 | 8/2003 | Szapiro et al. |
| 6,626,309 B1 | 9/2003 | Jansen et al. |
| 6,638,244 B1 | 10/2003 | Reynolds |
| 6,650,929 B1 | 11/2003 | Nemoto et al. |
| 6,681,946 B1 | 1/2004 | Jansen et al. |
| 6,716,193 B1 | 4/2004 | Neftel |
| 6,729,370 B2 | 5/2004 | Norton et al. |
| 6,743,214 B2 | 6/2004 | Heil et al. |
| 6,802,828 B2 | 10/2004 | Reynolds |
| 6,808,511 B2 | 10/2004 | Pond |
| 6,817,987 B2 | 11/2004 | Vetter et al. |
| 6,852,103 B2 | 2/2005 | Fowles et al. |
| 6,912,800 B2 | 7/2005 | Vetter et al. |
| 7,036,288 B2 | 5/2006 | Vetter et al. |
| 7,074,216 B2 | 7/2006 | Fowles et al. |
| 7,077,835 B2 | 7/2006 | Robinson et al. |
| 7,081,109 B2 | 7/2006 | Tighe et al. |
| 7,134,782 B2 | 11/2006 | Coffeen et al. |
| 7,137,974 B2 | 11/2006 | Almasian et al. |
| 7,161,488 B2 | 1/2007 | Frasch |
| 7,213,702 B2 | 5/2007 | Takimoto et al. |
| 7,331,941 B2 | 2/2008 | Vetter et al. |
| 7,338,477 B2 | 3/2008 | Meyer et al. |
| 7,452,344 B2 | 11/2008 | Jorgensen et al. |
| 7,470,257 B2 | 12/2008 | Norton et al. |
| 7,470,258 B2 | 12/2008 | Barker et al. |
| 7,553,304 B2 | 6/2009 | Neftel |
| 7,713,239 B2 | 5/2010 | Uber, III et al. |
| 7,731,678 B2 | 6/2010 | Tennican et al. |
| 7,736,353 B2 | 6/2010 | Reynolds |
| 7,753,891 B2 | 7/2010 | Tennican et al. |
| 7,824,373 B2 | 11/2010 | Kim et al. |
| 7,963,951 B2 * | 6/2011 | Kitani et al. .............. 604/248 |
| 2002/0002354 A1 | 1/2002 | Vetter et al. |
| 2002/0022804 A1 | 2/2002 | Connolly et al. |
| 2002/0061281 A1 | 5/2002 | Osbakken et al. |
| 2002/0065490 A1 | 5/2002 | Heinz et al. |
| 2002/0068896 A1 | 6/2002 | Robinson et al. |
| 2002/0087118 A1 | 7/2002 | Reynolds et al. |
| 2003/0069545 A1 | 4/2003 | Arm |
| 2003/0114798 A1 | 6/2003 | Langley et al. |
| 2003/0225378 A1 | 12/2003 | Wilkie et al. |
| 2004/0122345 A1 | 6/2004 | Muller |
| 2004/0232171 A1 | 11/2004 | Bobst |
| 2006/0027523 A1 | 2/2006 | Van Lintel et al. |
| 2006/0178642 A1 | 8/2006 | Gillespie et al. |
| 2006/0275336 A1 | 12/2006 | Du Plessis |
| 2006/0278588 A1 | 12/2006 | Woodell-May |
| 2007/0249996 A1 | 10/2007 | Tennican et al. |
| 2008/0015496 A1 | 1/2008 | Hamedi-Sangsari |
| 2010/0114067 A1 * | 5/2010 | Trieu et al. .............. 604/518 |

FOREIGN PATENT DOCUMENTS

| | | |
|---|---|---|
| JP | 3009662 | 2/1995 |
| WO | WO 96/29113 A | 9/1996 |
| WO | WO 99/37233 A1 | 7/1999 |
| WO | WO 00/13723 A | 3/2000 |
| WO | WO 01/41666 A1 | 6/2001 |
| WO | WO 2004/064706 A | 8/2004 |
| WO | WO 2006/044236 A2 | 4/2006 |

OTHER PUBLICATIONS

TW 096103375 Search Rept and OA, Nov. 12, 2012, Hyprotek, Inc.
EP 06839806 Search Report, Feb. 7, 2011, Hyprotek, Inc.
WO PCT/US05/036071 IPRP, Jan. 26, 2007, Hyprotek, Inc.
WO PCT/US05/036071 SearchReport, Sep. 8, 2006, Hyprotek, Inc.
WO PCT/US05/036071 WrittenOpinion, Sep. 8, 2006, Hyprotek, Inc.
WO PCT/US06/060745 IPRP, Jan. 26, 2011, Hyprotek, Inc.
WO PCT/US06/060745 SearchReport, Apr. 11, 2008, Hyprotek, Inc.
WO PCT/US06/060745 WrittenOpinion, Apr. 11, 2008, Hyprotek, Inc.
WO PCT/US08/078774 IPRP, Dec. 15, 2010, Hyprotek, Inc.
WO PCT/US08/078774 SearchReport, Dec. 17, 2008, Hyprotek, Inc.
WO PCT/US08/078774 WrittenOpinion, Dec. 17, 2008, Hyprotek, Inc.
Clip'n Ject, retrieved online Nov. 9, 2005: http://www.westpharma.com/products/clip_n_Ject.asp?1=0.
Debioclip Manual, retrieved online Nov. 9, 2005: http://www.debiotech.com/products/drugdd/debioclip.html.
http://www.duoject.com/flash/duoject.html (2 pages), Mar. 2, 2006.
http://www.life-assist.com/setfinder/preslit.html, ICU Medical/Setfinder Needle Free Products, pp. 1-5, Apr. 11, 2005.

* cited by examiner

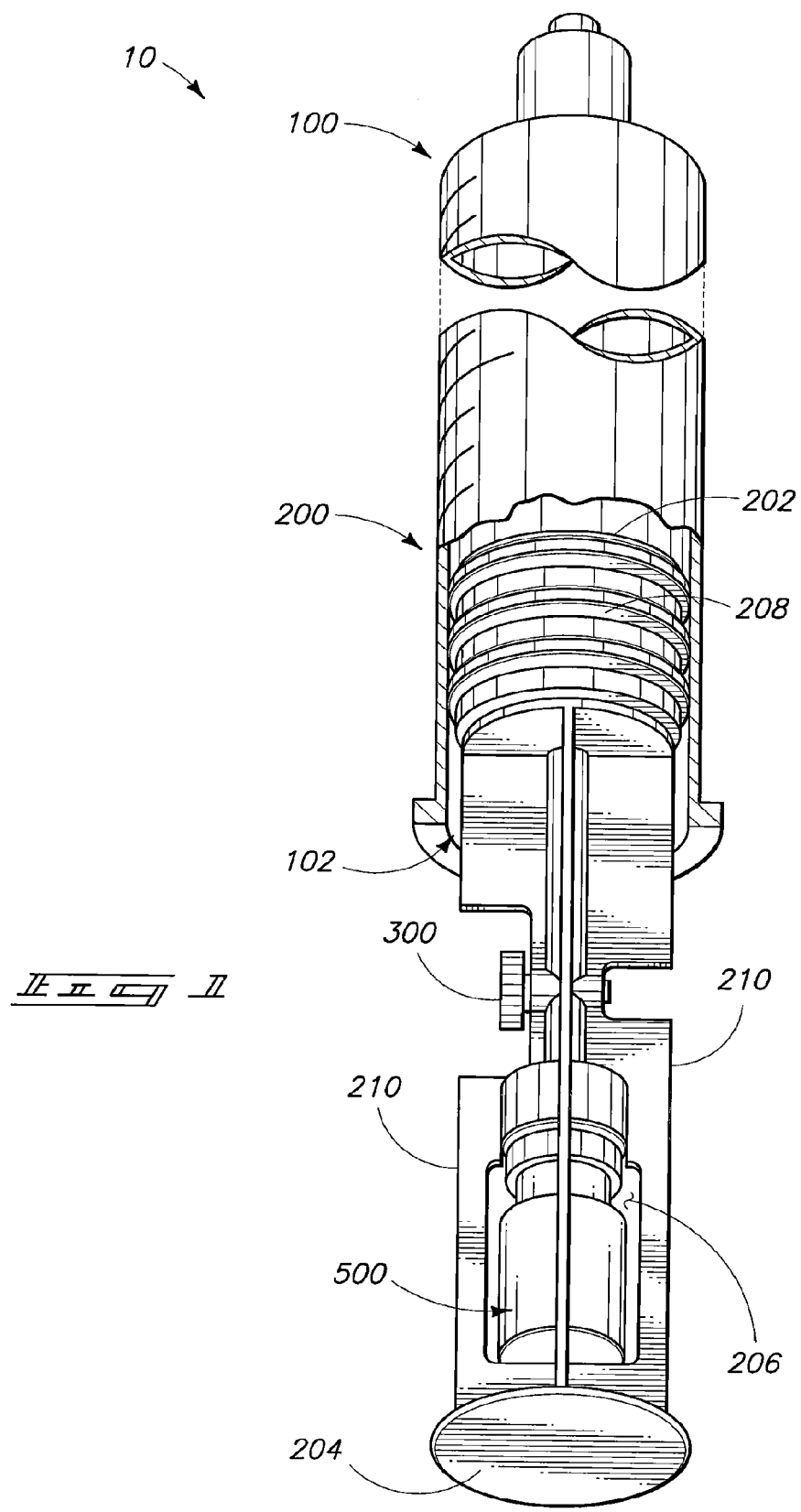

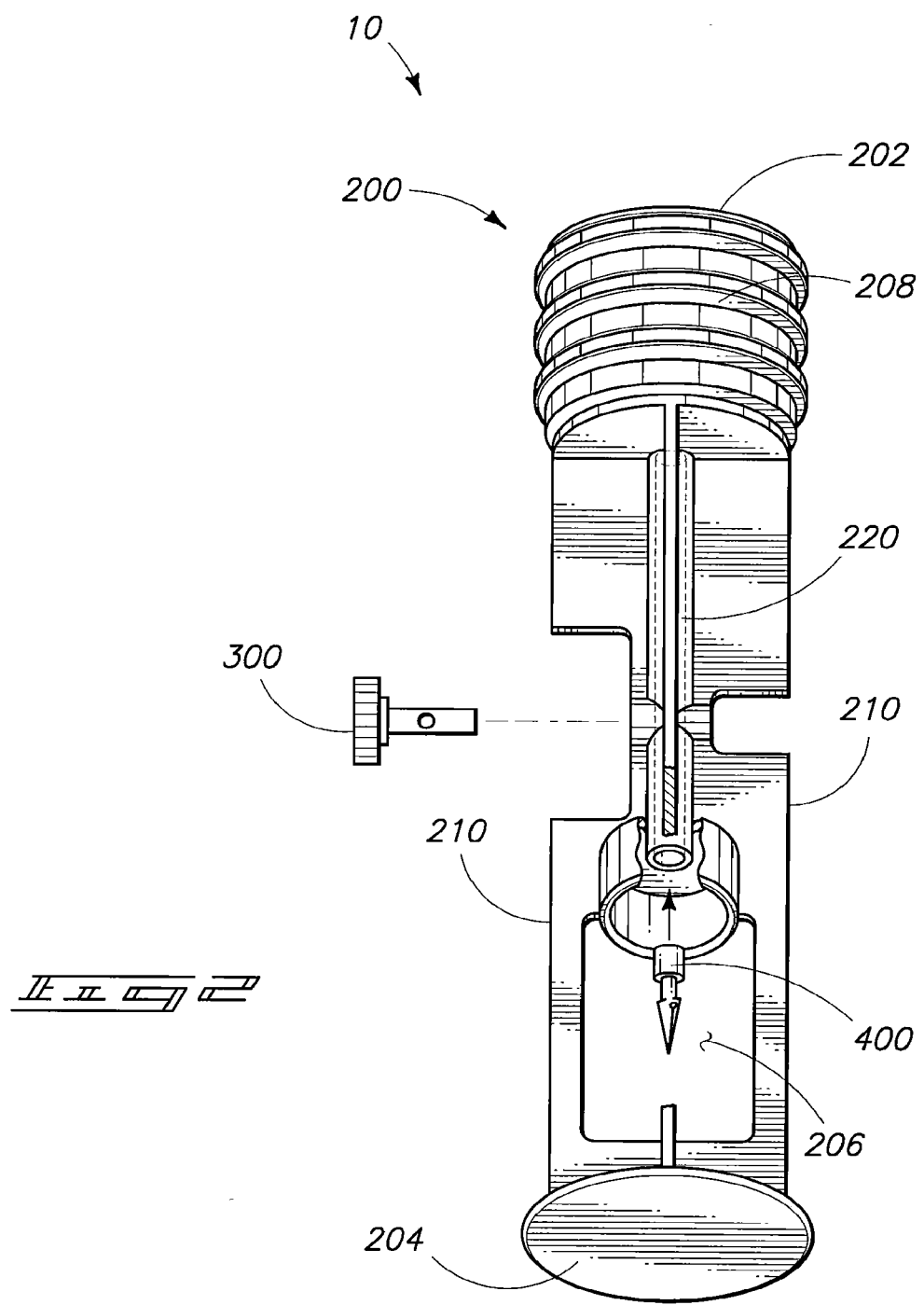

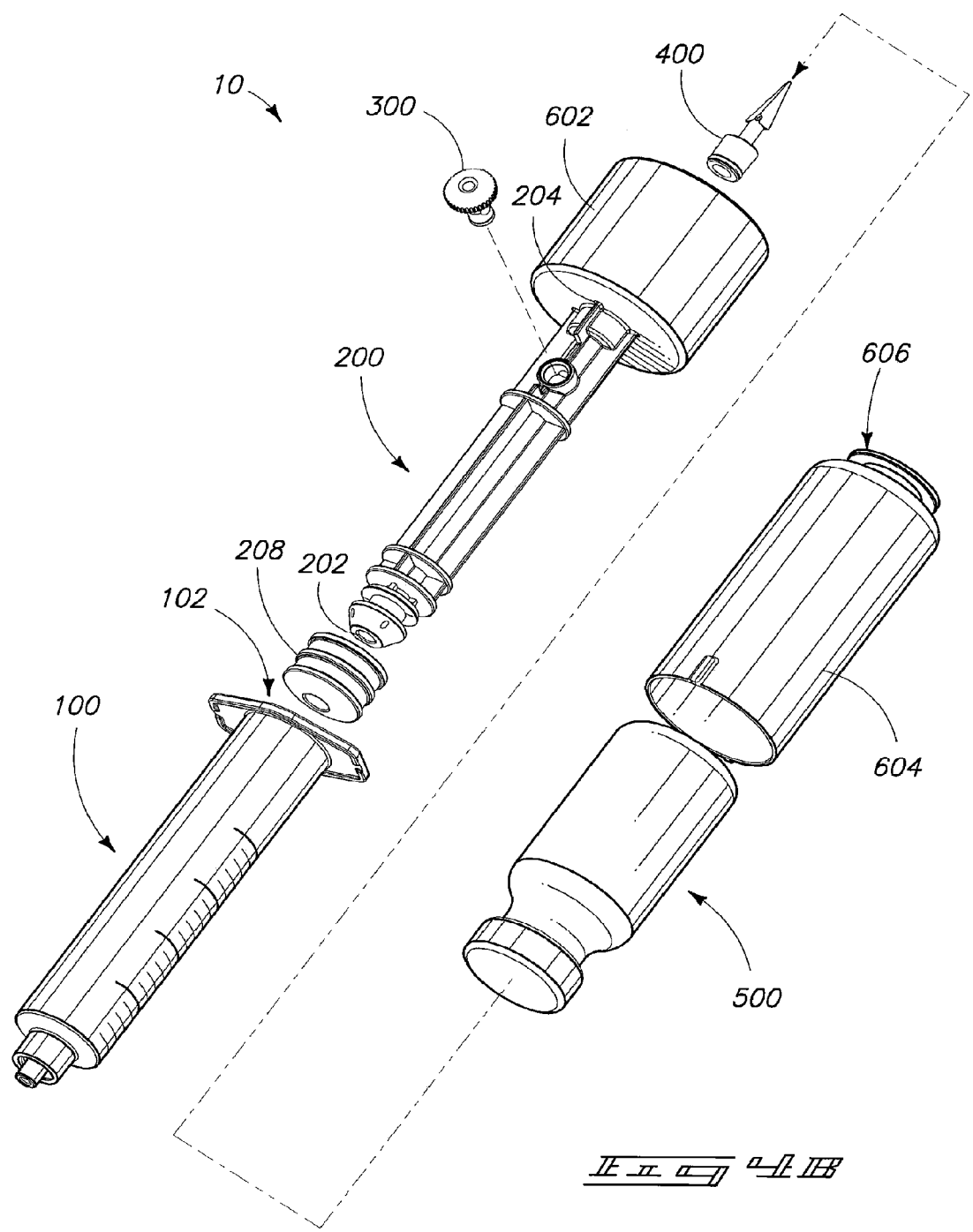

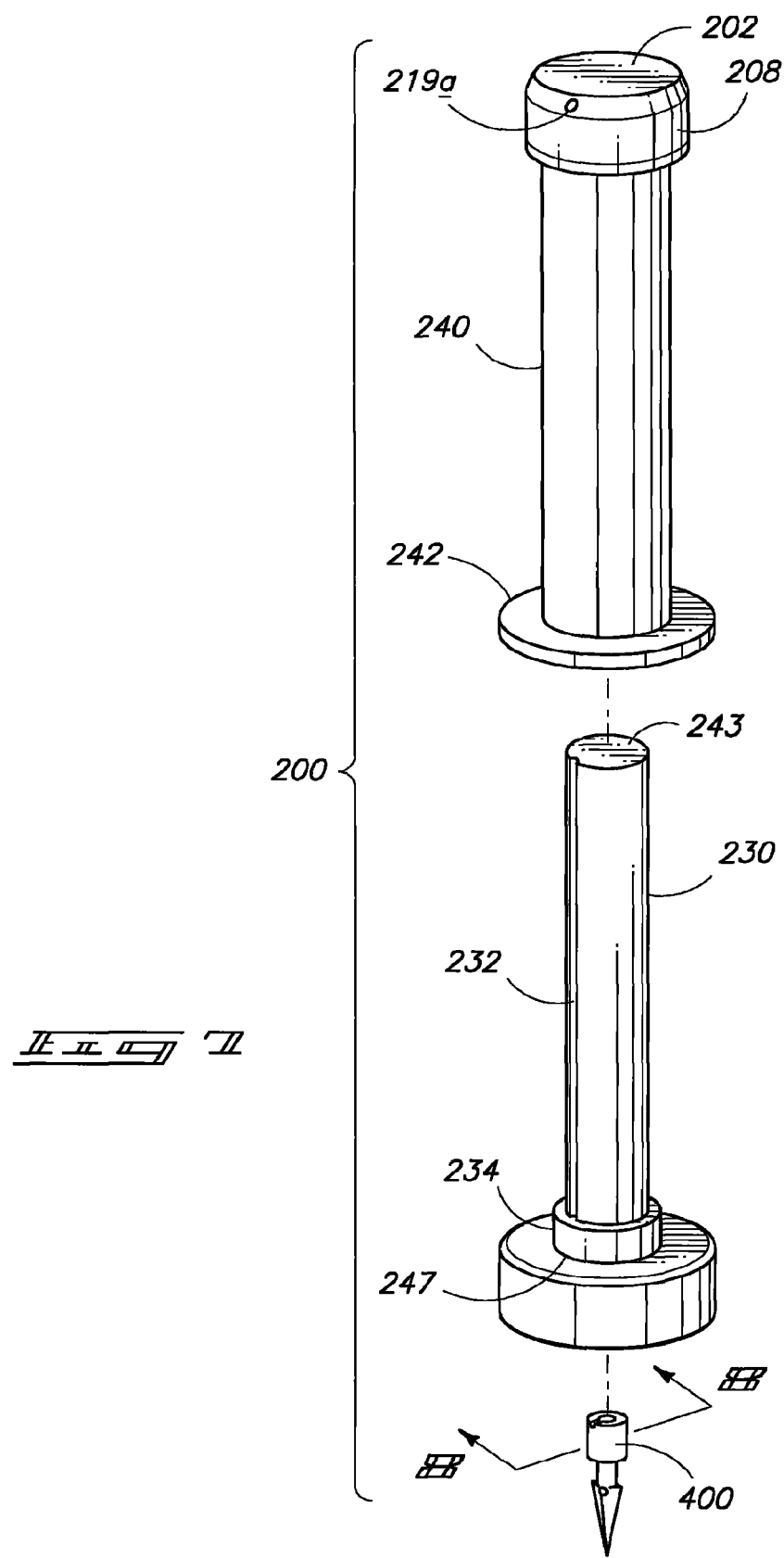

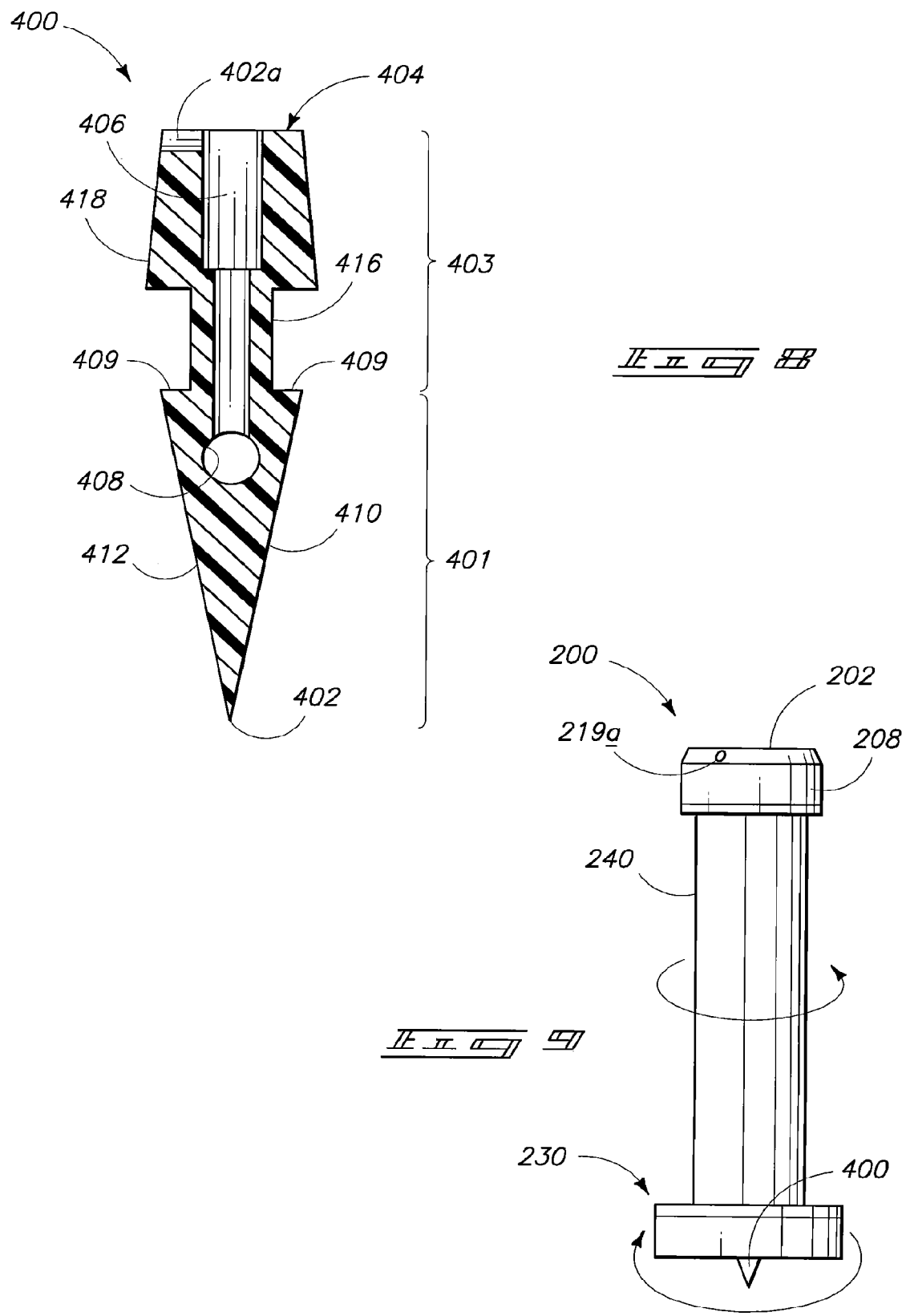

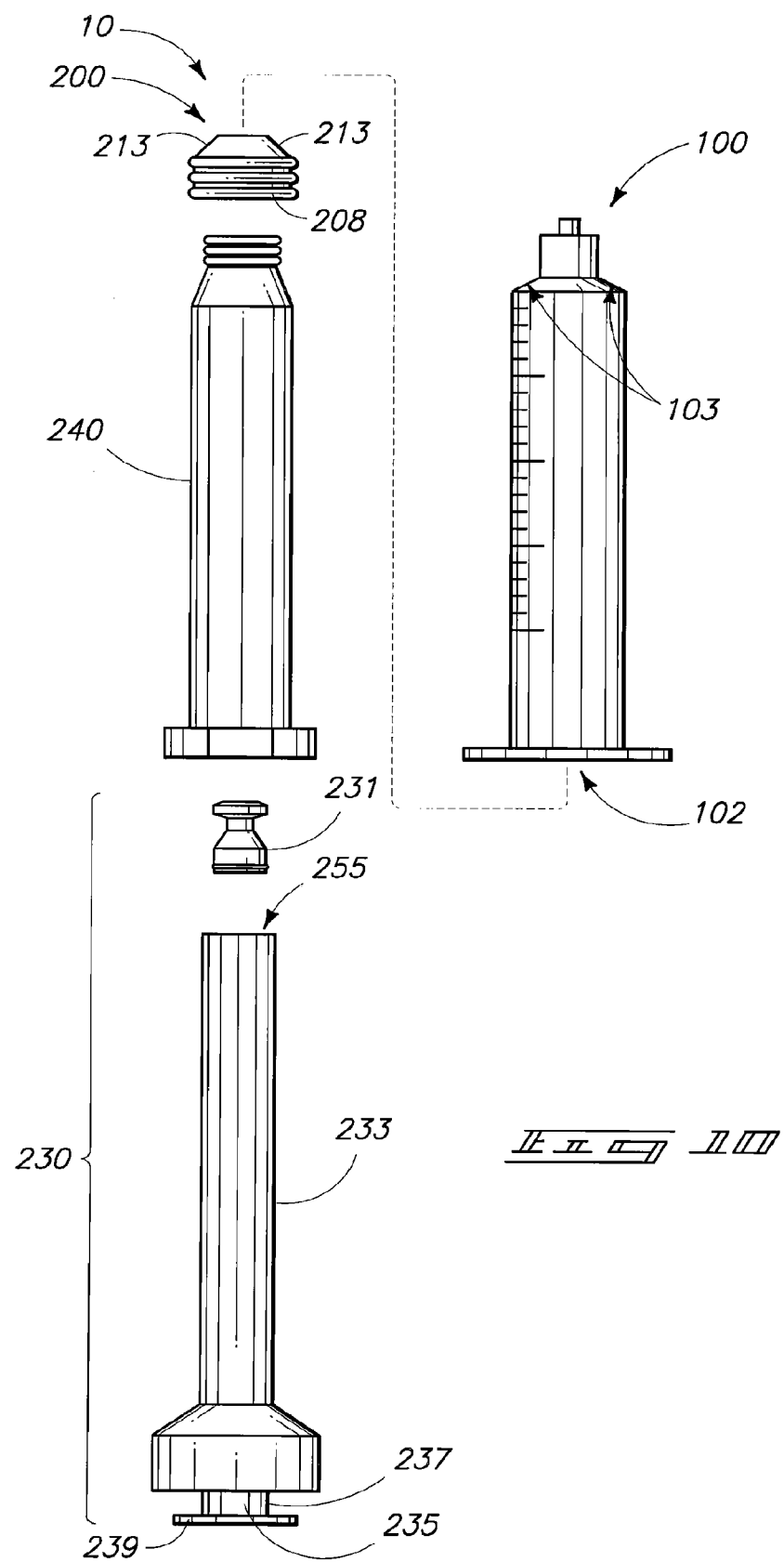

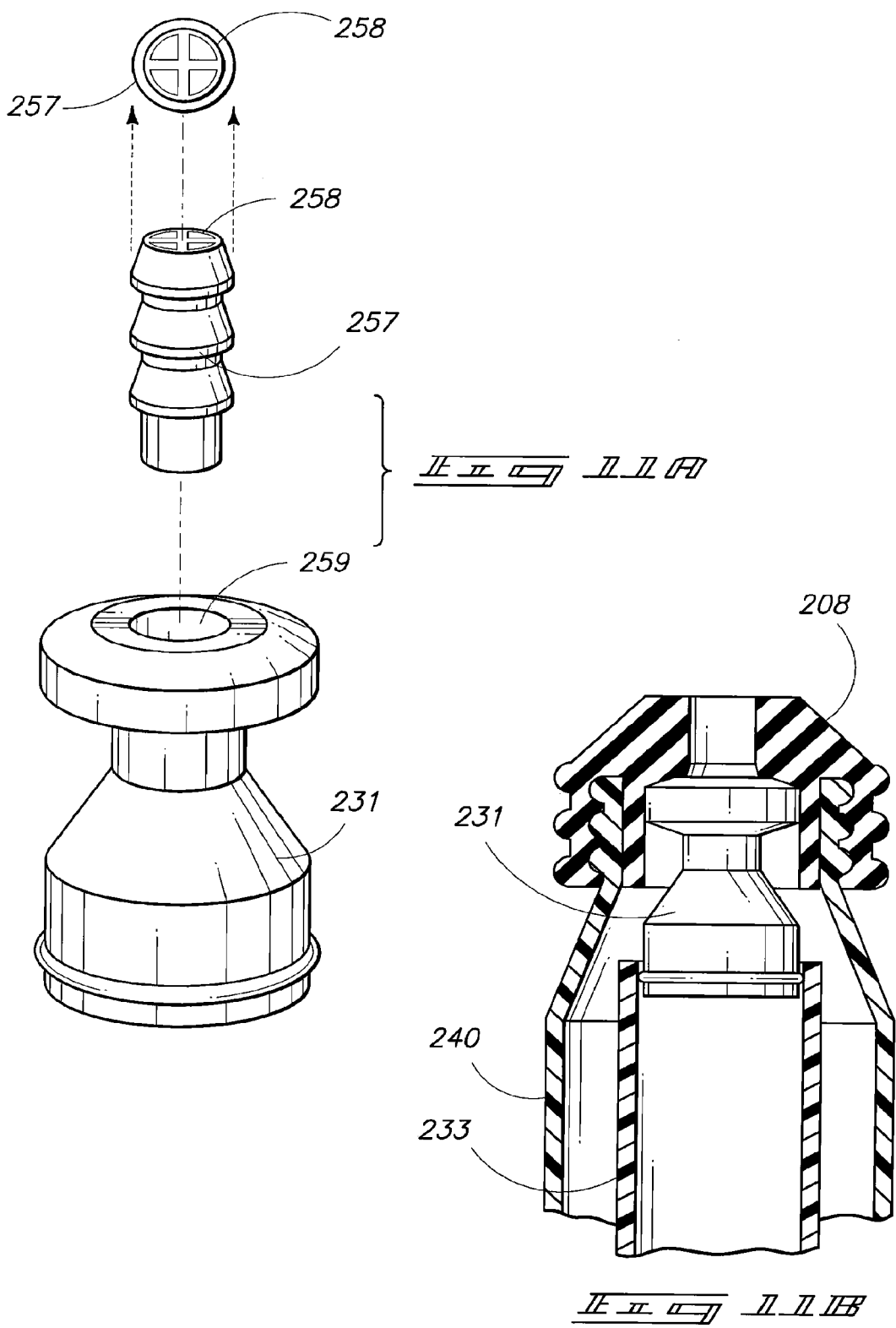

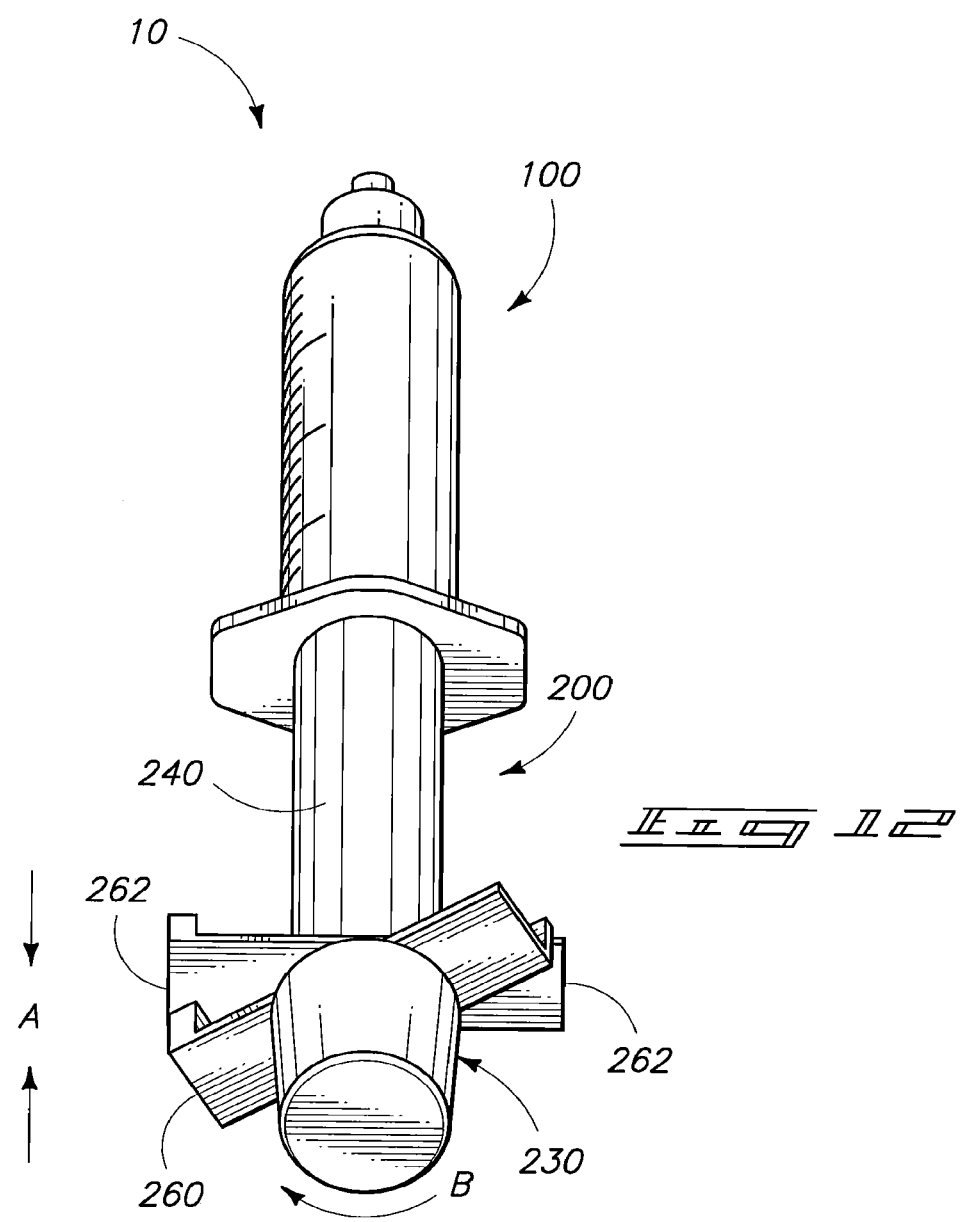

SYRINGE DEVICES, COMPONENTS OF SYRINGE DEVICES, AND METHODS OF FORMING COMPONENTS AND SYRINGE DEVICES

RELATED PATENT DATA

This application is a continuation of U.S. patent application Ser. No. 11/558,146 which was filed Nov. 9, 2006, which claims priority under 35 U.S.C. §119 to U.S. Provisional Application No. 60/735,481, which was filed Nov. 9, 2005; and claims priority to U.S. Provisional Application No. 60/763,647, which was filed Jan. 30, 2006, the entirety of each of which are incorporated herein by reference.

TECHNICAL FIELD

Embodiments of the invention pertain to syringe devices, syringe piston configurations, medication agent preparation systems and methods of preparing a medication agent.

BACKGROUND OF THE INVENTION

Preparation of medicants or medication agents and administration of such agents to an individual often involves mixing of two or more components to form the agent and subsequent delivery of the mixed medicant to the individual. The mixing of components can typically involve extraction of one component in fluid form from a vial or other container and transfer of such components into a separate container which holds another component. In particular instances, only a portion of the contents of a vial or container is to be utilized for preparing a mixture prior to administering. Accordingly, the extraction and transfer can involve precise measuring of one or more components to be mixed.

A variety of problems may occur when utilizing conventional methodology and devices for mixing and/or administering medicants to an individual. For example, where multiple components are to be mixed, extraction and transfer of one component and introduction of such component into another component can potentially expose one or both of the components to a non-sterile or contaminated environment leading to contamination of the resulting medicant. Additionally, incomplete extraction or improper measurement of one or more components can result in preparation and/or administration of an improper dosage. In particular instances, once a medicant is mixed the mixture must again be extracted from a vial or container into a syringe prior to administering to an individual. Such additional transfer can lead to additional opportunities for contamination, incomplete extraction of contents and/or inaccurate measuring of a component or the resulting medicant.

In practice, there is limited availability of sterile environments for maintaining sterility during transfer and/or mixing of components, or preparation and transfer of medicants. Additional errors can result from use of the wrong diluent to reconstitute the medication. Finally, preparation of medicants utilizing multiple components can be tedious and time consuming due to factors such as the need to access individually packaged items such as separate vials and/or transfer devices, or to measure one or more components to be combined to form the medicant.

It would be desirable to develop alternative methodology and systems for preparation and administration of medicants.

SUMMARY OF THE INVENTION

In one aspect the invention encompasses a syringe device. The device includes a syringe barrel and piston having a first end insertable within the syringe barrel. A second end of the piston opposes the first end and the piston has an overall length defined between the first and second ends. A vial port is disposed within the piston and is configured to receive a vial in lengthwise orientation along a portion of the overall length of the piston. A fluid passageway extends through the piston from the vial port through the first end of the piston.

In one aspect the invention encompasses a syringe piston having a stem portion which includes one or more projections. A sealed portion is over-molded onto the stem portion and covers the one or more projections.

In another aspect the invention encompasses a syringe device having a syringe barrel and a syringe piston having a first end insertable within the syringe barrel and a second end opposing the first end. A vial housing is associated with and extends from the second end of the piston. A piercing structure is associated with the second end of the piston and extends into the vial housing.

In one aspect the invention encompasses a syringe device including a syringe barrel, a piston sleeve and a sleeve insert. The sleeve insert has a first end insertable within the sleeve and an opposing second end. The sleeve insert has a length defined by the distance between the first and second ends. A fluid channel extends along an exterior side of the sleeve insert from the first end at least a portion of the length of the sleeve insert. A rotary valve controls fluid communication between the fluid channel and the syringe barrel.

In one aspect the invention encompasses a syringe device having a syringe barrel and a piston sleeve with a sleeve insert having a first end insertable within the sleeve and an opposing second end with a length of the sleeve insert being defined by the distance between the first and second ends. A compartment is disposed within the sleeve insert and a valve controls fluid communication between the compartment and the syringe barrel.

In another aspect the invention encompasses a medication agent preparation system. The system includes a syringe having a syringe barrel with an internal chamber, a piston having a first end, a second end and a fluid passageway passing longitudinally through the piston, at least a portion of the piston including the first end being inserted within the chamber. A valve is associated with the fluid passageway and includes a valve body and a cap over-molded onto the valve body.

The invention additionally encompasses a method of preparing a medication agent for administration to an individual. A syringe is provided having a syringe barrel and a piston disposed at an initial position relative to the syringe barrel. The piston has a piston sleeve and a sleeve insert. A first component is provided within the syringe barrel and a second component is provided within a vial. A valve is associated with the fluid passageway between the vial and the barrel of the syringe. The valve is initially in a closed position blocking fluid passage through the passageway. The method includes repositioning the valve and sliding the piston to join the first and second components. The first and second components are mixed to form a medication agent and the agent is drawn into the syringe barrel.

In a further aspect the invention includes a method of preparing a composition including providing a syringe barrel having a barrel chamber containing a first component and providing a piston having a compartment containing a second component. The piston includes a piston sleeve and a sleeve insert. The sleeve insert includes a tip and a body with a seal that is over-molded onto the tip and an end of the piston sleeve. The seal has at least one opening passing therethrough. The method includes rotating the piston sleeve relative to the sleeve insert to establish fluid communication between the compartment and the barrel chamber. The piston is slid to join the first and second components and the first and second components are mixed to form a composition. The composition is drawn into the syringe chamber.

BRIEF DESCRIPTION OF THE DRAWINGS

Preferred embodiments of the invention are described below with reference to the following accompanying drawings.

FIG. 1 is a side view and partial cross-sectional view of a mixing assembly in accordance with one aspect of the invention.

FIG. 2 is a side view and partial cross-sectional view of a portion of a syringe device in accordance with one aspect of the invention.

FIG. 4B is an exploded view of the assembly shown in FIG. 4A.

FIG. 7 is an exploded side view of another syringe piston configuration in accordance with one aspect of the invention.

FIG. 8 is a side view of a piercing device in accordance with one aspect of the invention.

FIG. 9 is a side view of the FIG. 7 piston device in an assembled configuration.

FIG. 10 is an exploded side view of an alternative mixing assembly in accordance with another aspect of the invention.

FIG. 11A is an exploded side view of a portion of the system shown in FIG. 10.

FIG. 11B is an enlarged cross-sectional view of a portion of the assembled form of the system depicted in FIG. 10.

FIG. 12 is a side view of the assembled device shown in FIG. 10 having alternative features.

DETAILED DESCRIPTION OF THE PREFERRED EMBODIMENTS

Figure 3A:
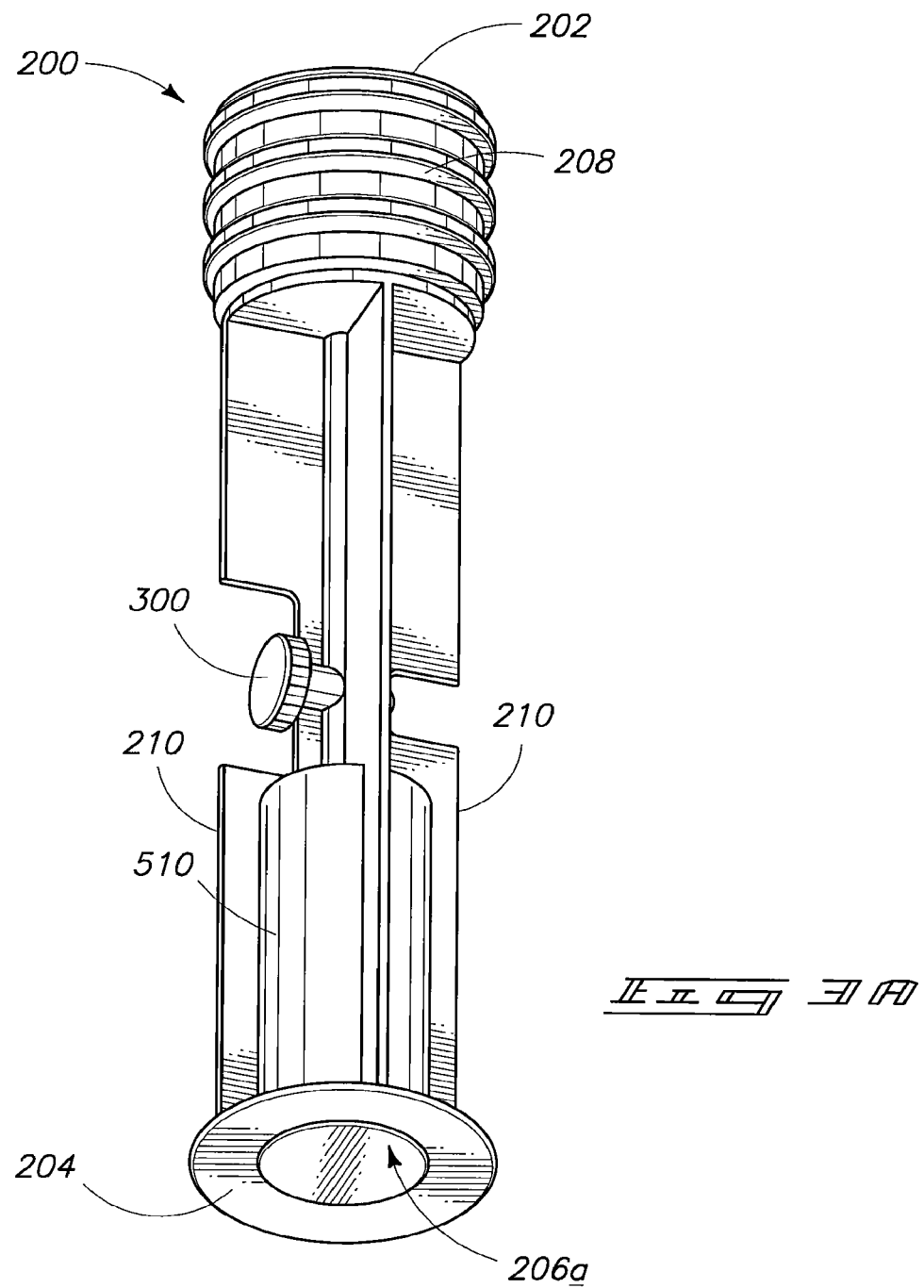
FIG. 3A is a side view of a portion of a syringe device with a slidable housing disposed in a first position.

This disclosure of the invention is submitted in furtherance of the constitutional purposes of the U.S. Patent Laws "to promote the progress of science and useful arts" (Article 1, Section 8).

In general the invention provides methodology and devices for combining and mixing components to produce a mixture and encompasses device configurations to allow such combining and mixing to occur without contamination or exposing of the components or mixed agents to a non-sterile environment. In particular, methodology of the invention involves combining and mixing components to produce an administration ready agent such as a medicant and in particular aspects includes administering such agent to an individual. Accordingly, device configurations of the invention allow combination of separate components such that the combined and mixed components are administration-ready. The general concepts and example devices in accordance with the invention are illustrated in the accompanying FIGS. 1-12.

The device components and methods described and exemplified herein can be utilized in conjunction with, or alternative configurations of, the devices and methods described in U.S. patent application Ser. No. 11/238,880 which was filed Sep. 28, 2005 (henceforth the earlier filed application). Accordingly, the specification and figures from such earlier filed application are hereby incorporated by reference. It is to be understood that many of the concepts of the present invention can be utilized in conjunction with or can be adapted to other device configurations including conventional syringe devices and components, those described in the earlier application and those yet to be developed.

Where devices in accordance with the invention are used for preparation of a medicant, the devices are preferably closed-system mixing assemblies. An example of a mixing assembly 10 in accordance with the invention is illustrated in FIG. 1. Mixing assembly 10 can comprise a syringe body (or barrel) 100 and a piston 200 that has a fluid passageway longitudinally through a portion of its length (discussed further below). In some instances a reversibly attached cap (not shown) may be present providing a fluid seal at a forward end of the syringe body.

Piston 200 has a first end 202 and an opposing second end 204 defining an overall length of the piston. A valve 300 is associated with the fluid channel which passes through a portion of the length of the piston. A vial port 206 is disposed along a segment of the length of the piston stem and is configured to receive a vial 500 lengthwise within the vial port. Preferably the fluid passageway through the piston extends from the vial port through first end 202.

Piston 200 further includes a seal 208 which is able to form a slidable fluid tight seal between the internal walls of the syringe body and the sidewalls of the piston seal. Valve 300 can be configured to selectively control fluid communication between the syringe chamber and vial 500.

Referring to FIG. 2, such illustrates a fluid passageway 220 extending from first end 202 through seal 208 and lengthwise through the piston to vial port 206. A piercing device 400 can be associated with fluid channel 220 and can extend into port 206. An example piercing device can be as described in the earlier filed application. Piercing device 400 can have a fluid channel passing therethrough and can be configured to puncture the vial septum and be retained across the septum establishing fluid communication between the interior of the vial and fluid passageway 220.

Vial port 206 can be formed by removal of all or a portion of one or more piston fins 210. Preferably enough fin structure is retained to allow vial retention and stabilization within port 206.

Valve 300 can be, for example, a two-way valve as illustrated or can be an alternative valve type as described in the earlier filed application.

For the syringe assembly shown in FIGS. 1 and 2, the device is preferably initially provided in a configuration in which the vial is sealed and disposed in a non-contact position relative to piercing structure 400. In preparation for use the vial can be repositioned to contact piercing device 400 and slid within the port allowing device 400 to puncture and cross the septum. Valve 300 can then be repositioned to an 'on' position establishing fluid communication between the vial and the syringe chamber. Sliding of the piston relative to the syringe can be utilized to combine syringe contents with vial contents. The two components can be mixed by repeated sliding of the piston or by agitation of the device. The mixed components can then be drawn into the syringe and the valve closed in preparation for administration of the prepared agent.

Referring to FIG. 3A, an alternative intra-piston vial port configuration is illustrated. Features of the illustrated device in common with the earlier described piston are numbered identically. Features that are additional or different relative to the earlier device are denoted by a letter appendage or with a unique numeric identifier.

Figure 3B:
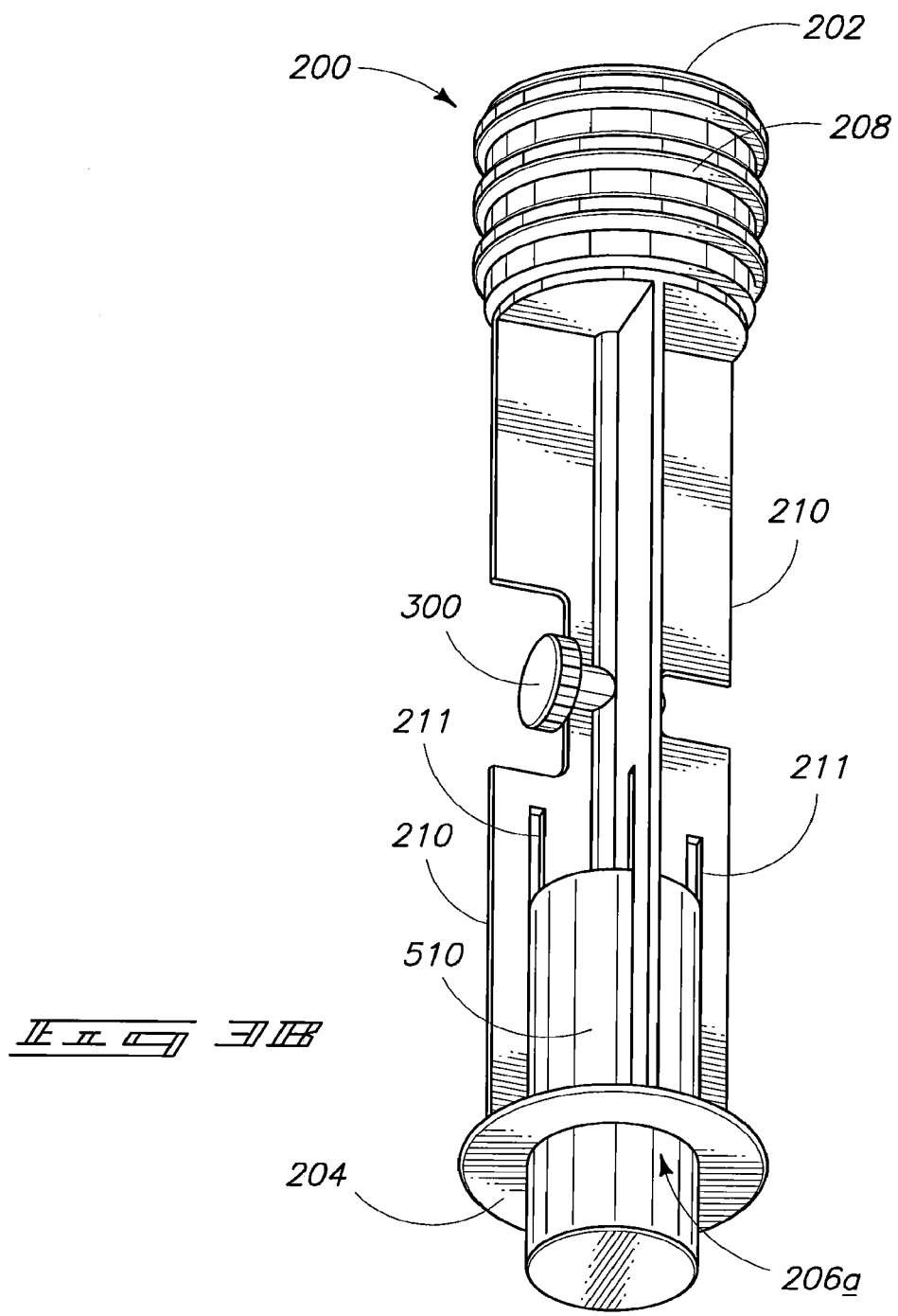
FIG. 3B is a side view of the portion of the syringe device of FIG. 3A shown with the slidable housing disposed in a second position.

The illustrated piston 200 has an internal passageway extending from first end 202 to an intra-piston vial port 206a. The intra-stem vial port is configured to receive a vial housing 510 which can house a vial (not shown). Such vial housing can be insertable through an opening in second end 204 of the piston. Referring to FIG. 3B, a plurality of receiving slots 211 can be configured to guide and position housing 510 within the vial port. Piston 200 can comprise a piercing structure (not shown) associated with the vial port and the fluid passageway. Piston 200 can preferably be initially provided such that housing 510 and a vial received internally within the housing are disposed in a non-contact position such that the piercing device does not contact or penetrate the vial lid or septum. During preparation for use the vial housing and internal vial can be slid toward first end 202 to allow penetration of the vial septum or cap by the piercing device thereby establishing fluid communication between the interior of the vial and the fluid passageway of the piston. Fluid passage through the passageway can be selectively controlled by valve 300. Preparation of a medication agent for administration to an individual can be performed by providing an associated syringe (not shown), and utilizing methodology analogous to that described above for the device depicted in FIG. 1.

Figure 4A:
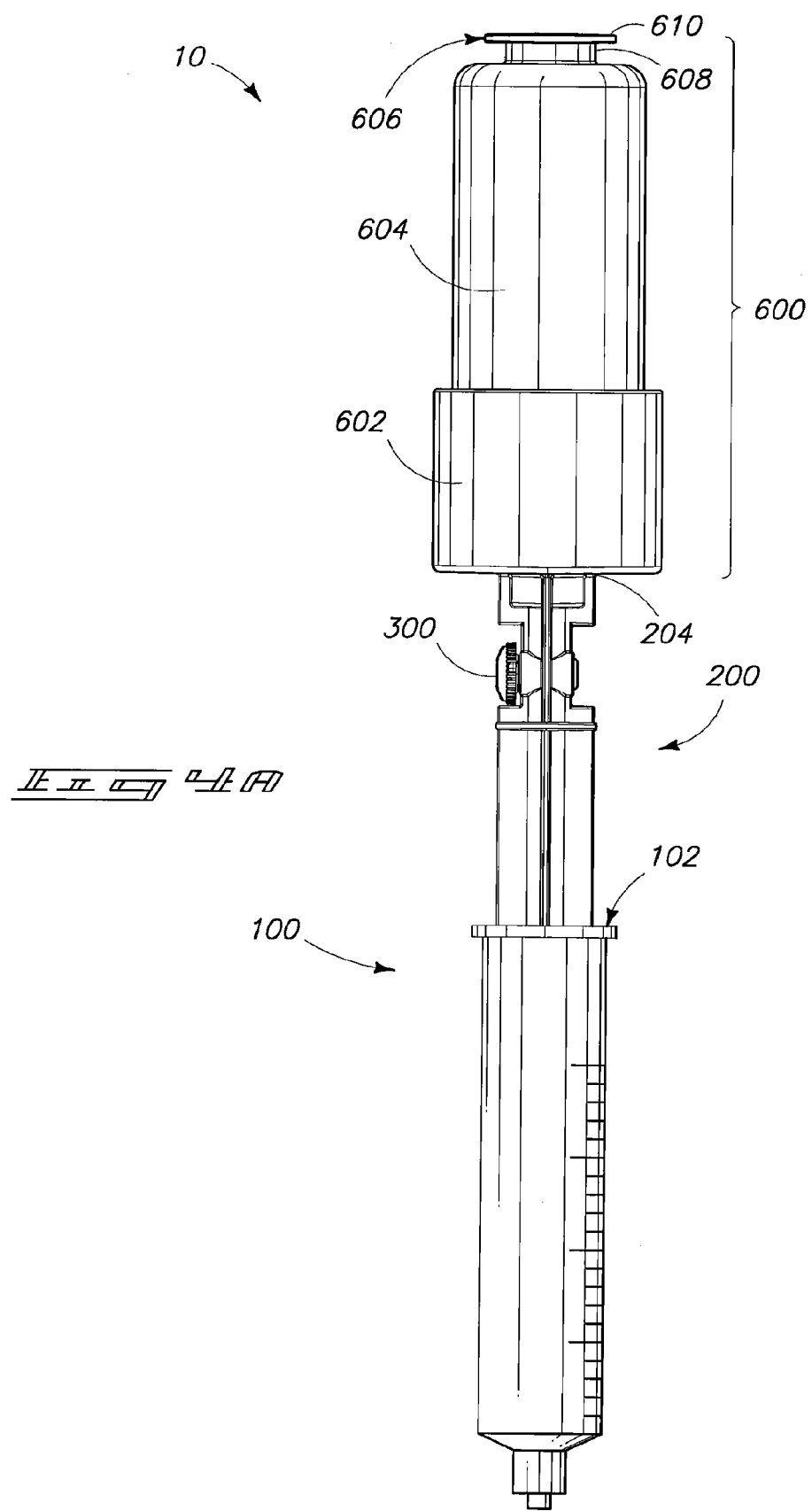
FIG. 4A is a side view of a mixing assembly in accordance with one aspect of the invention.

Another alternative configuration of the invention is described with reference to FIGS. 4A-4B. Referring initially to FIG. 4A, a piston 200 is illustrated insertable within a syringe 100 having an internal chamber 102. Syringe piston 200 has an internal passageway passing longitudinally such that the passageway traverses the length of the piston. Fluid passage through the passageway is selectively controlled by valve 300 associated with such passageway.

As illustrated, a first end 202 (see FIG. 4B) is inserted within the syringe barrel and a vial housing 600 is associated with second end 204 of the piston. Vial housing 600 can comprise, for example, two parts 602 and 604. First part 602 can, in particular instances, be an extension of piston 200. Housing part 602 can be integral with, permanently attached to or reversibly attached to piston 200. A second portion 604 of the vial housing can be configured to be joinable to first portion 602 such that a vial inserted within the container can be completely enclosed within the housing. Such enclosure of a medicant vial can prevent vial breakage and can advantageously avoid removal and improper replacement of the vial and/or inadvertent substitution of the vial with another vial possibly containing an improper diluent or other agent.

Joining of the second part 604 of the housing to the first part of the housing can comprise, for example, inserting a portion of part 604 into the first part, inserting a portion of part 602 within part 604, threading of one of the two parts into the other of the two parts, and/or use of other appropriate fittings or joining techniques. In particular embodiments, part 604 can preferably be configured to be stabilized in a first position and can be further extended within the second part to a second position upon application of force (sliding, twisting or other force based upon the design of the particular fitting configuration utilized). Such configuration can allow an enclosed vial to be moved from a first "non-contact" position relative to a piercing device (see FIG. 4B) into a second "access" position where the piercing device is able to pierce a vial septum or other vial cover and thereby provide access to vial contents.

In particular implementations the vial housing portion can have an adaptor appendage 606 configured to adapt the syringe device for use in conjunction with a syringe pump. Such appendage can preferably include a stem 608 protruding from part 604, where the stem has a first diameter. Stem portion 608 extends to a disk structure 610 where the disk structure has a diameter greater than the stem structure and is configured for insertion into a slot in a piston driver of a syringe pump. Such configuration can allow devices in accordance with the invention to be utilized in a conventional syringe pump. The presence of the insertable disk, when inserted into a slot of the piston driver of the syringe pump, can prevent inadvertent advancement of the plunger when the pump is off. Devices of the invention can alternatively be manually manipulated.

Referring to FIG. 4B, such shows an exploded view of the device depicted in FIG. 4A. These figures illustrate the association of piercing device 400 which can be at second end 204 of piston 200 and can extend into first part 602 of the vial housing. FIG. 4B additionally illustrates an alternative placement of valve 300 with respect to the overall length of piston 200. It is to be understood that the placement of valve 300 along the length of the piston is not limited to any particular location and that the depicted locations are for purposes of illustration only.

As further illustrated in FIG. 4B a seal 208 can be mounted on first end 202 of syringe piston 200. Seal 208 preferably has an outer diameter along at least a portion of its length that forms a fluid seal between the chamber walls and the seal. Where piston 200 comprises an internal fluid passageway, seal 208 can preferably have one or more openings to allow fluid communication between the internal passageway of the piston and the syringe chamber.

The mixing/administration system 10 depicted in FIGS. 4A-4B can initially be provided in a "non-contact" position where piercing structure 400 does not puncture the cap or septum of vial 500. In a particular configuration, positioning of container parts 602 and 604 with respect to one another can be stabilized utilizing a plastic shrink-wrap at least at the junction of the two housing parts. The shrink-wrap can provide a sterile retainer and prevent inadvertent or unintentional engagement of the piercing device with the vial septum. Positioning can also or alternatively utilize a tack weld or molded attachment stabilization where a breakable attachment is provided that can be broken by application of force (twisting, sliding or other force depending upon the particular containment configuration and positioning of the breakable attachment(s)). The two-part container portion of the described syringe device configuration can be formed utilizing materials such as plastic materials, preferably hard plastic materials. Spot welding or tacking can be achieved utilizing, for example, RF welding, microwave welding, heat welding or other appropriate plastic welding.

Another aspect of the invention is described with reference to FIGS. 5A-5C. In general, this aspect of the invention involves over-molding of elastomeric seal portions onto hard plastic body pieces of various parts of devices in accordance with the invention. Over-molding involves molding of an overlying part directly onto an underlying supporting part. It is to be understood that over-molding can be utilized with alternative piston and valve bodies in addition to those specifically described in this particular aspect of the invention. Alternative piston and valve bodies can include, for example, alternative pistons and valves described herein, pistons and valves described in the earlier filed application, conventional pistons and valves and piston, and valve configurations yet to be developed.

Figure 5A:
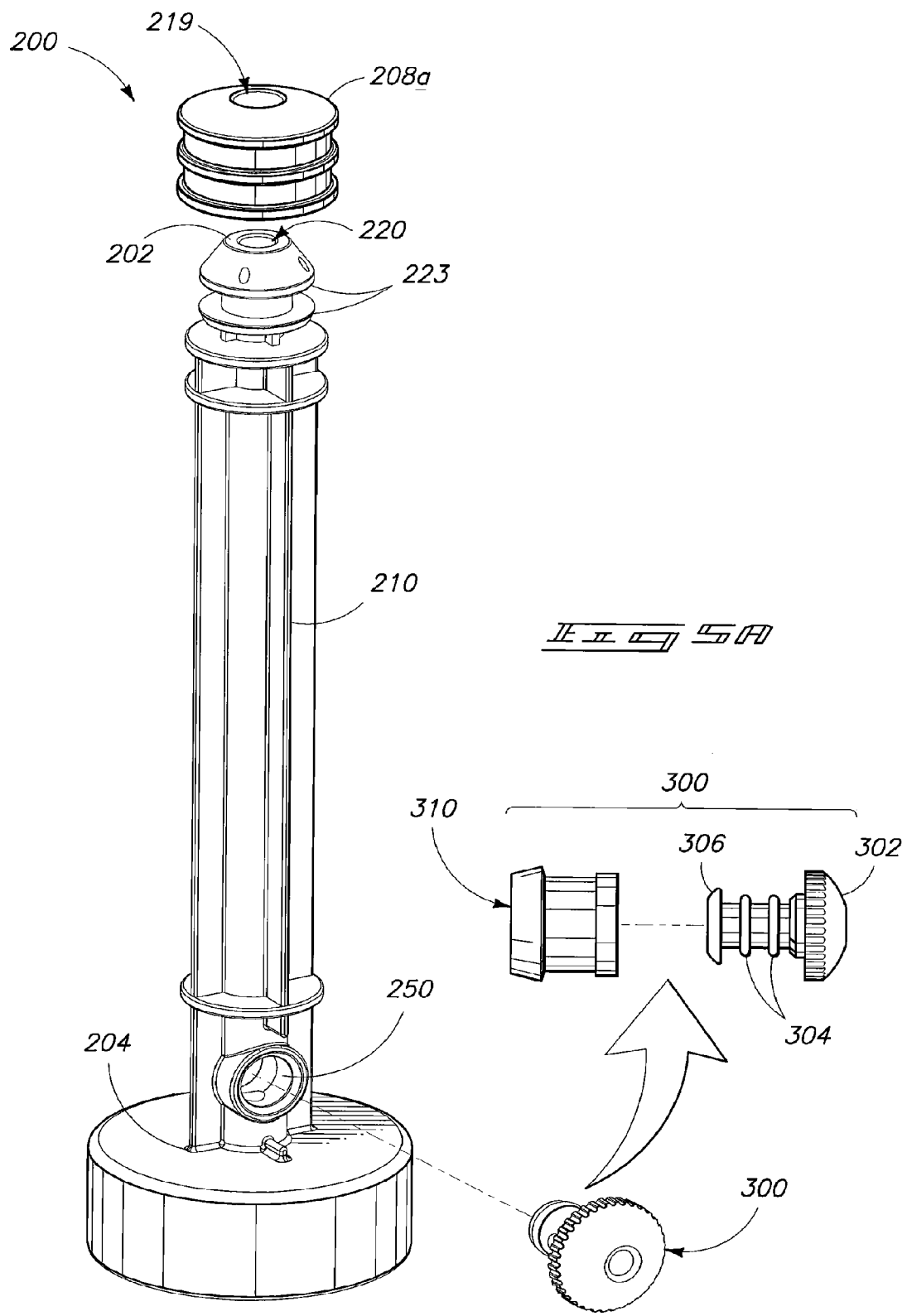
FIG. 5A is an exploded side view of a syringe piston in accordance with one aspect of the invention.

Referring initially to FIG. 5A, a piston 200 is illustrated having a valve 300 configured to fit into an opening 250, and having a channel 220 extending longitudinally through the piston. A piston seal 208a is illustrated having an opening 219 which extends through the seal. Although FIG. 5A illustrates piston 200 in an exploded view, it is to be understood that seal 208a is permanently attached to the piston during the over-molding process.

Piston 200 preferably has at least one projection 223 disposed at or near first end 202 of the piston. The projection or projections can advantageously support the over-molded seal and can assist in retaining the seal on the first end of the piston. Where the piston is configured to have a fluid passageway or channel passing longitudinally therethrough, the over-molding process can preferably provide the over-molded seal to have one or more openings extending through the seal to provide fluid communication between the passage through the piston and the internal region of an associated syringe body.

The over-molding process utilized can be adapted for various syringe body designs such that the over-molded seal has a forward end which is shaped to conform to the taper/shape of the interior of the syringe body at the forward end of the syringe body. The seal can preferably be molded to provide a seal diameter to allow insertion and movement of the seal within the syringe chamber while providing a fluid seal along the chamber sidewalls. In particular aspects, the diameter/size of the seal mold can be modified to produce seals that fit varying syringe barrel sizes without varying the piston size/diameter.

In a similar aspect, valve 300 can comprise a valve body 302 and an over-molded valve cap 310. Valve body 302 can preferably have one or more projections 304, 306 configured to support and retain the over-molded cap 310.

Valve 300 can be, for example, a push-pull type valve as illustrated in FIG. 5A. In the configuration shown, the push-pull valve body has a larger projection 306 at the inserted end of the valve. The presence of the large projection can provide a shape configuration to assist in positioning and/or retaining the valve within the port when pulling the valve into an open position. It is to be understood that the invention contemplates utilization of alternative valve types such as, for example, a rotatable valve having an opening passing through the body and the over-molded seal.

Valve cap 310 and seal 208a can comprise, for example, elastomeric materials. The elastomeric materials utilized can be the same or can differ from one another. Similarly, piston 200 and valve body 302 can be formed of hard plastic materials and can be the same or can differ relative to one another. Examples of elastomeric materials that can be utilized include, but are not limited to, polyurethanes, polypropylene-EPDM, other polypropylenes, polysiloxane and/or silicone materials, butyl materials, isoprenes, neoprenes, polyethylenes and various copolymers, composites, blends or other combinations of such materials. Examples of plastics that can be utilized for piston and/or valve body formation include, but are not limited to, polyethylenes, polypropylenes, polycycloolefines, polyvinyl chlorides (PVC), polyamides (including aliphatic and aromatic variants), polyesters, polycarbonates, polyacrylates, polyurethanes, copolymers, blends, composites and combinations thereof.

Figure 5B:
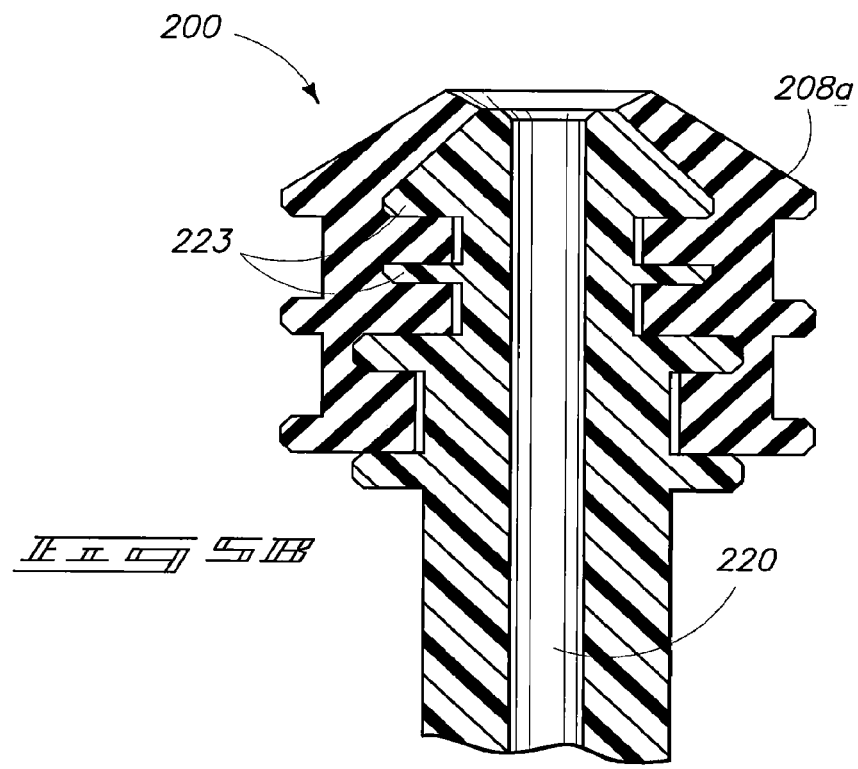
FIG. 5B is an enlarged fragmentary view of the assembled syringe device shown in FIG. 5A.
Figure 5C:
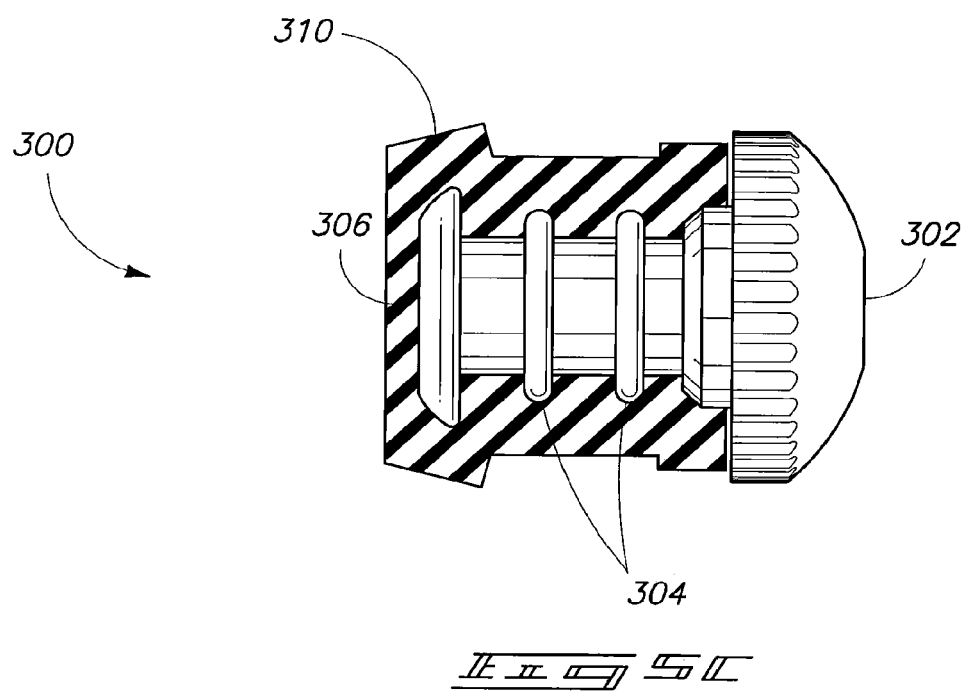
FIG. 5C is a side view of an assembled portion of the syringe piston shown in FIG. 5A.

Turning to FIG. 5B, such illustrates over-molded seal 208a on piston 200 supported by projections 223. Also illustrated is channel 220 passing longitudinally through the piston and passing through seal 208a. Referring to FIG. 5C, such illustrates over-molded cap 310 on valve body 302 supported by projections 304 and 306.

Where over-molding is utilized to form pistons and/or valves in accordance with the invention, the stem/body portions can be fabricated in a first process and the over-molded seal/cap portion can be formed in a second process. The over-molding will form the seal/cap directly onto the body or stem portion. The over-molding can occur directly after formation of the underlying part or the underlying part can be formed initially and can be removed from the corresponding mold, transferred and/or stored prior to the over-molding process.

The over-molding process can advantageously avoid manual assembly of the piston or body with respect to the cap or stopper. Additional advantages of providing an over-molded elastomeric seal include minimization or prevention of fluid leakage between the seal and the underlying piston, and a secure attachment such that the seal does not pull away from the underlying piston during piston rotation relative to the syringe or drawing of the piston within the syringe. Additionally, the seal can be configured to have a thin wall across the first end of the piston. Relative to conventional piston seals, the thin wall of the over-molded seal can decrease the piston rebound and thereby minimize the reflux of fluid back through the tip of the syringe. Further, the seal can be molded to have a central protrusion on the front face (not shown) configured to insert at least partially into the fluid passage through the syringe tip to further minimize fluid retained in the syringe. This feature can be especially advantageous for administration of costly medical agents.

Figure 6:
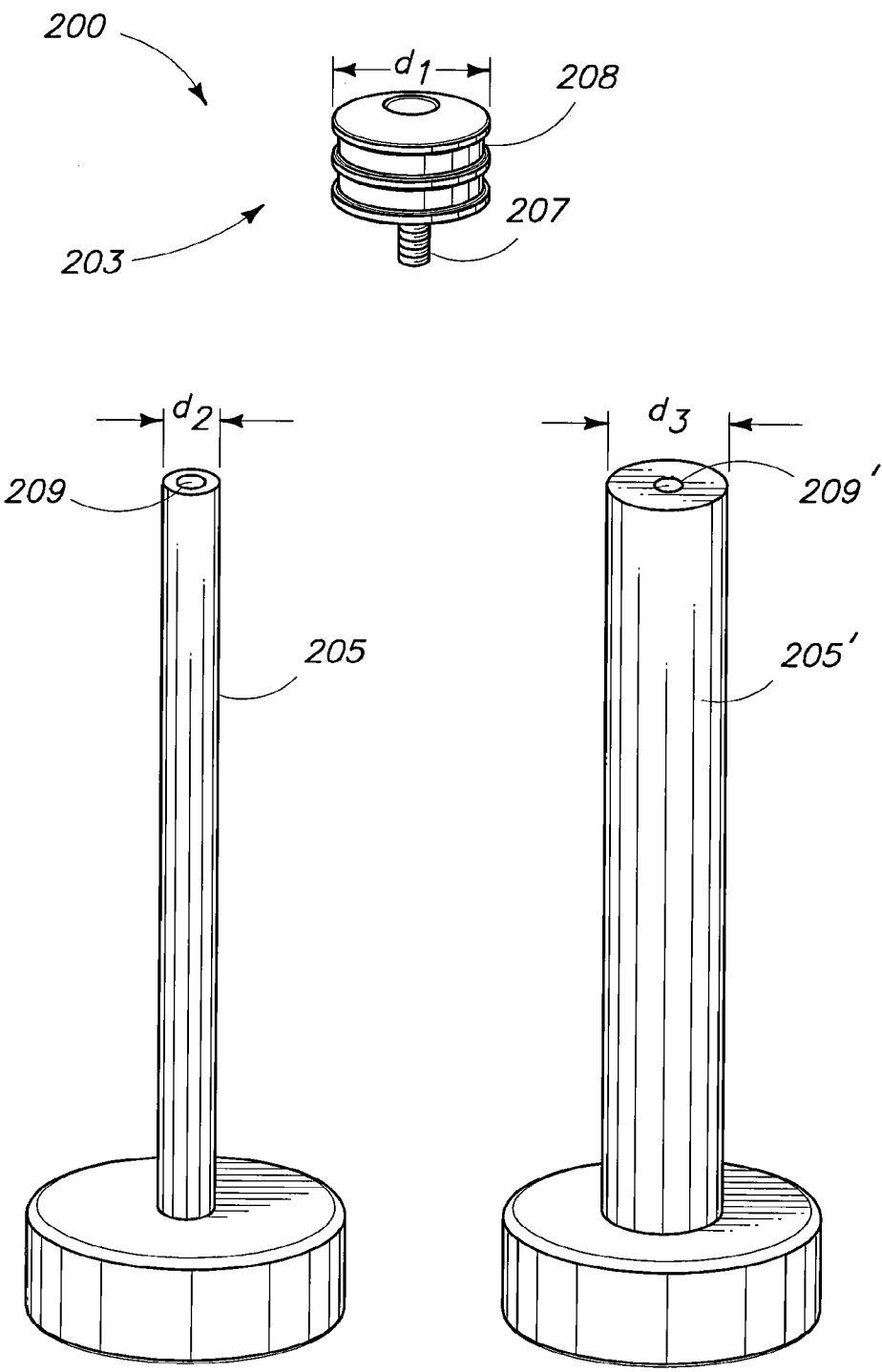
FIG. 6 is a side view of a syringe piston in accordance with one aspect of the invention having a tip portion connectable to alternative stem portions.

Referring to FIG. 6, over-molding can also be utilized in conjunction with a multipart piston configuration. In this aspect a piston seal 208 can be over-molded onto a piston tip 203 which can be threaded or otherwise attached to alternative piston stems 205, 205'. Stems 205 and 205' and tip 203 can have internal fluid passageways or can alternatively be solid core pieces. Tip 203 can be joined to a piston stem 205 or 205' by insertion of an attachment portion of the tip into an opening 209 of the stem 205 or 205'. In particular configurations the joining can utilize threading, snap-locking, press-fitting, application of an appropriate adhesive or other appropriate joining techniques.

The over-molded seal 208 can be molded to have a diameter '$d_1$' which can vary depending upon the diameter of the syringe body (not shown) that will be utilized. The tip along with the over-molded seal can be joined with a piston of an appropriate diameter (e.g. $d_2$ or $d_3$) for use with the particular syringe barrel. Accordingly, a single tip configuration can be utilized for a wide range of seal, syringe barrel and piston sizes.

Another embodiment of the invention is described with reference to FIGS. 7-9. Referring initially to FIG. 7, piston 200 can include a piston sleeve 240 and a sleeve insert 230 configured to insert within sleeve 240. Sleeve portion 240 can have a seal 208 mounted on first end 202. The seal can have an opening 219a which passes through the side of the seal and aligns with a similar opening which passes through sleeve portion 240. Sleeve 240 can additionally have a base ring 242 or other base structure to allow manipulation of the sleeve.

Sleeve insert 230 can comprise a channel 232 passing from a first end 243 of the piston insert along an outside surface of the insert and through a collar 234 at opposing end 247 of the insert. A piercing structure 400 can be provided in association with second end 247 of the piston insert. Referring to FIG. 8, such shows the detail configuration of an example of a piercing device configuration that can be utilized in association with the piston illustrated in FIG. 7.

The piercing structure 400 depicts an illustrative piercing structure in accordance with the invention. Piercing structure 400 can be described as having a head segment 401 comprising a tip 402 disposed at a first end. Piercing structure 400 additionally has a stem/body portion 403 which extends from head portion 401 to a base surface 404 disposed at a second end of the structure opposing the first end. A channel 406 or alternative fluid passageway extends through the base surface and preferably through an entirety of body portion 403.

Piercing structure 400 can preferably comprise an opening 402a which aligns with channel 232 of insert 200 upon seating of the piercing structure in association with piston 200.

The piercing structure shown in FIG. 8 is an illustrative shape and form. In a preferred aspect of the invention channel 406 extends less than an entirety of an internal length of head segment 401 such that the channel does not pass through tip 402. Rather, one or more access holes 408 are provided, for example, through one or both of the external surfaces of the head portion. Configurations of the piercing structure where the channel does not pass through the tip can advantageously minimize or prevent coring of a septum material or plugging of the channel during a piercing operation. Additional aspects pertaining to piercing structures are set forth in the earlier filed application.

Referring next to FIG. 9, such illustrates the piston device shown in FIG. 7 in an assembled configuration. Sleeve insert 230 is inserted within sleeve portion 240. Insert 230 can be rotated relative to sleeve portion 240 to allow the two parts of the device to function as a rotatable valve. Typically, first end 202 of the assembled structure will be inserted within a syringe barrel (not shown). The device can initially be provided with an accompanying vial such that the vial septum is intact. In preparation for administration of a medicinal agent, piercing structure 400 can be utilized to pierce the vial septum. Rotation of insert 230 relative to sleeve 240 can be utilized to align the fluid channel of the insert with opening 219a through the piston seal and the corresponding opening through the piston sleeve. Such alignment can establish fluid communication between the syringe chamber and the vial. Subsequent combining and mixing of medication components can be performed as described above. Upon completion of the mixing, the valve can be closed by rotation of the insert 230 relative to the sleeve. The administration-ready composition can then be administered or can be stored prior to administration.

Another mixing and administration system 10 having a multipart piston is depicted in FIGS. 10-12. Referring initially to FIG. 10, system 10 can include a syringe barrel 10 having an internal chamber 102. System 10 additionally includes a piston 200 inclusive of a piston sleeve 240 and a sleeve insert 230. Insert 230 can be described as having a stem portion 233, at least a portion of which is hollow to serve as a container 255. An insert cap portion 231 can be configured to attach to piston stem 233 thereby covering and enclosing container 255. An appendage 237 can extend from the piston insert. Appendage 237 can comprise a stem portion 235 and a disk portion 239 where disk portion 239 is configured to fit into a slot on a piston driver of a syringe pump.

Sleeve portion 240 can include a piston seal 208. Seal 208 can preferably be over-molded and can comprise a shape having tapered walls 213 that match the internal taper region 103 of syringe chamber 102.

Referring to FIG. 11A, cap portion 231 can be configured to provide valve action utilizing an inserted compression spring 257 and an overlying retainer 258. Cap 231 and retainer 258 can be formed of hard plastic materials such as those described above. Spring 258 can be formed of an elastomeric material such as those elastomeric materials set forth above.

Referring next to FIG. 11B, in the illustrated embodiment over-molded seal 208 can be over-molded onto piston sleeve 240 and also onto cap 231. The internal valve spring and the retainer are provided prior to the over-molding process. Once the over-molding process is complete, stem portion 233 can be positioned by insertion of the stem within sleeve portion 240. The internal container of insert 233 will typically contain a component of a medicinal agent such as, for example, a lyophilized powder, at the time of insertion into the sleeve. Cap 231 and stem portion 233 can preferably be configured to include a snap fitting, press fitting or other appropriate joining configuration such that, once joined, the cap and stem portions do not pull apart upon drawing back of the piston.

FIG. 12 shows an assembled device analogous to the device shown in FIG. 10 and having additional optional features. As illustrated, piston 200 comprising sleeve 240 and insert 230 is inserted within a syringe barrel 100. Sleeve 240 can comprise extension tabs 262 and insert 230 can also comprise extension tabs 260. The extension tabs present on the sleeve and the insert can assist in manipulation of the valve associated with the piston. Squeezing together of the tabs in the A direction can open the valve. Rotation of the insert relative to the sleeve (direction B) can then be performed to position the tabs to "lock" the sleeve and insert position relative to one another thereby locking the valve into the open position. To close the valve the insert can be rotated in an opposing direction and tabs 260 can be moved apart relative to tabs 262.

Preparation of an administration ready agent utilizing the device depicted in FIG. 12 can be performed in a manner analogous to that described above with the exception that the internal container within insert 230 replaces the earlier described vial. The mixing/administration system 10 shown in FIG. 12 can additionally include an appendage associated with the piston and opposing syringe 100 where such appendage is configured to allow insertion into a slot of a piston driver of a syringe pump.

Packaging of the devices of the embodiments described herein can utilize conventional packaging techniques, or can utilize the packaging techniques described in the earlier filed application, adapted for the specific device being packaged.

The features and embodiments described herein can be combined with one another where appropriate, and can be utilized in conjunction with features and embodiments disclosed in the earlier filed application. The features and embodiments of the invention are suitable or adaptable for use in combination with conventional syringe components, vials, and devices, as well as those yet to be developed.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

The invention claimed is:

1. A syringe device comprising:
   a syringe barrel;
   a piston sleeve insertable in the syringe barrel;
   a sleeve insert having a first end insertable within the sleeve, an opposing second end, and a length defined by the distance between the first and second ends, the sleeve insert further comprising a vial housing disposed on the second end of the sleeve insert;

a fluid channel extending along an exterior side of the sleeve insert from the first end at least a portion of the length of the sleeve insert, the fluid channel in fluid communication with an interior of the vial housing; and a rotary valve controlling fluid communication between the fluid channel and the syringe barrel, wherein the rotary valve is configured to establish fluid communication between the syringe barrel and the fluid channel by rotation of the sleeve insert relative to the piston sleeve.

2. The syringe device of claim 1 further comprising a piston seal over-molded onto the piston sleeve.

* * * * *